United States Patent
Dennig et al.

(10) Patent No.: US 8,222,030 B2
(45) Date of Patent: Jul. 17, 2012

(54) METHOD FOR THE SEPARATION OF LIVING CELLS

(75) Inventors: Jörg Dennig, Langenfeld (DE); Silvia Magyar, Solingen (DE); Christoph Erbacher, Haan (DE); Ralf Himmelreich, Langenfeld (DE); Ralf Peist, Düsseldorf (DE)

(73) Assignee: Qiagen GmbH, Hilden (DE)

( * ) Notice: Subject to any disclaimer, the term of this patent is extended or adjusted under 35 U.S.C. 154(b) by 901 days.

(21) Appl. No.: 11/990,856

(22) PCT Filed: Aug. 24, 2006

(86) PCT No.: PCT/EP2006/065660
§ 371 (c)(1),
(2), (4) Date: Sep. 3, 2008

(87) PCT Pub. No.: WO2007/023181
PCT Pub. Date: Mar. 1, 2007

(65) Prior Publication Data
US 2009/0023205 A1    Jan. 22, 2009

(30) Foreign Application Priority Data
Aug. 24, 2005   (DE) .................. 10 2005 040 259

(51) Int. Cl.
*C12N 1/02*    (2006.01)

(52) U.S. Cl. .............. 435/325; 435/308.1; 435/180
(58) Field of Classification Search .............. 435/325, 435/308.1, 180
See application file for complete search history.

(56) References Cited

FOREIGN PATENT DOCUMENTS

| WO | WO 97/11160 | 3/1997 |
|---|---|---|
| WO | WO 99/07749 | 2/1999 |
| WO | WO 01/30995 A1 | 5/2001 |
| WO | WO 03/035888 A1 | 5/2003 |
| WO | WO 2005/014801 A1 | 2/2005 |
| WO | WO 2005/066361 | 7/2005 |

OTHER PUBLICATIONS

Gjessing et al. Adsorption, Simple Binding and Complex Binding of Rat Hepatocytes to Various in Vitro Substrata. Experimental Cell Research 129 (1980) 239-249.*
Suehiro, J., et al., "Dielectrophoretic Filter for Separation and Recovery of Biological Cells in Water," *IEEE Transactions on Industry Applications* 39:1514-1521 (2003).

* cited by examiner

*Primary Examiner* — Taeyoon Kim
(74) *Attorney, Agent, or Firm* — Fanelli Haag & Kilger PLLC

(57) ABSTRACT

The present in invention relates to a method for the separation of living cells from a mixture of dead and living cells which optionally can also possibly contain cell fragments.

7 Claims, 3 Drawing Sheets

METHOD FOR THE SEPARATION OF LIVING CELLS

RELATED APPLICATIONS

This application is the U.S. National Phase under 35 U.S.C. §371 of International Application No. PCT/EP2006/065660, filed on Aug. 24, 2006, which in turn claims the benefit of German Application No. 10 2005 040 259.3, filed on Aug. 24, 2005, the disclosures of which Applications are incorporated by reference herein.

The present invention relates to an improved method for the separation of living cells from a mixture that in addition to living cells optionally can contain dead cells and other components such as cell debris.

The isolation and purification of cell populations has for a long time been a dominant theme in many areas of cell biology. Thus, during the electroporation of eukaryotic cells, for example, significant cytotoxic effects occur that complicate many of the subsequent analytical methods. There is in general the need to separate directly the dead cells from the living cells, not only after electroporation, but after cell treatments that are carried out under cytotoxic conditions.

For many years methods for such cell separations have been known from the state of the art that are based inter alia on density centrifugation techniques—which depend on size and density—or, for example, on continuous flow electrophoresis techniques—which exploit the surface charge of the cells.

In addition to the separation or isolation of living cells by means of specific antibodies, procedures are known from the state of the art that exploit, for example, the tendency of apoptotic and necrotic cells to bind to a ligand—for example, annexin V—through the cell membrane, whereby the ligand itself can be coupled, for example, to a magnetic particle as solid carrier.

In addition, numerous density centrifugation separations for example have been known for many years that work with different substances to form density gradients. Commercial materials that can be used in these methods are inter alia Ficoll®, Percoll®, caesium chloride or dextran.

Although these materials can by all means be used for the separation of cells, they have various serious drawbacks that make them appear less suitable for the problem according to the invention. These disadvantages rest in part on the sensitivity of the cells towards a higher osmotic or ionic loading, as well as towards the gradient material used.

Thus one serious disadvantage of these methods is that the cells are subjected for a considerable period of time to the gradient material, which can be toxic or at least disadvantageous to the viability of the cells. This is particularly the case when gradient solutions are based on, for example, Ficoll®, Percoll® or dextran, which do not represent physiological solutions. As is known from the state of the art, Ficoll® is toxic for the cells and is moreover mutagenic. Percoll® is equally damaging to cells. In the concentrations used in gradient separations, dextran can cause cell damage as a result of the osmotic loading applied to the cells.

On the other hand, the available alternatives and the above-mentioned methods have also considerable disadvantages—they require, for example, multiple processing steps and are very elaborate and difficult to automate.

The problem of the present invention is thus to avoid at least in part the disadvantages of the methods known from the state of the art and to provide a method for the isolation of living cells which in particular does not rely on time-consuming and work-intensive centrifugation steps and which in particular allows an enrichment or isolation of living cells in the highest possible yield. A further problem is to provide a method that is easy to automate.

The problems previously described are solved by the method proposed in the present invention in which the cells to be separated, both living and dead, are brought into contact with a matrix which has a surface able to immobilise or absorb only the dead cells.

It was surprisingly found that dead cells are immobilised on polymers having polyanionic structures, in particular anionic polymers having functional groups of carboxylic acids or other acids—for example sulphonic or phosphonic acids, whereas living cells are not absorbed.

The cell material used here are advantageously cell types such as, for example, adherent cells and/or suspension cells. Particularly preferred are adherent primary cells or suspensions cells such as, for example, immune cells.

Suitable matrices for the solution of the problem according to the invention are in principle all polymers forming anionic structures, whereby carboxylated polymers, copolymers or terpolymers are preferred. For example, copolymers based on styrene, vinyl methyl ether, linear or branched alkenes can be used—such as, for example, 1-octadecene or isopropylene and maleic acid or acrylic acid, whereby the carboxyl function optionally can be esterified to different degrees. Cited as preferred polymers are, for example, the following alkyl acrylates: methyl acrylate, ethyl acrylate, vinyl acrylate, propyl acrylate, butyl acrylate, hexyl acrylate, octyl acrylate, decyl acrylate, dodecyl acrylate, myristyl acrylate, lauryl acrylate, cetyl acrylate, stearyl acrylate, methyl methacrylate, ethyl methacrylate, propyl methacrylate, butyl methacrylate, isobutyl methacrylate, hexyl methacrylate, 2-ethylhexyl acrylate, 2-ethylhexyl methacrylate, phenyl methacrylate, octyl methacrylate, decyl methacrylate, dodecyl methacrylate, myristyl methacrylate, lauryl methacrylate, cetyl methacrylate, of which methyl acrylate is particularly preferred.

The branched or linear $C_1$ to $C_{12}$ alkyl ester of acrylic acid or methacrylic acid are preferred.

$C_1$ to $C_{12}$ alkyl ester within the meaning of the present invention stands for an alkyl ester having one to twelve carbon atoms in the alkyl partial structure of the original alkanol part.

In general, within the meaning of the present invention—unless otherwise stated—$C_1$ to $C_6$ alkyl groups are preferred. $C_1$-$C_6$ alkyl—or in general: alkyl or alkyl residues—stand generally for a branched or linear hydrocarbon residue with 1 to 6 carbon atom(s) which optionally can be substituted by one or several halogen atoms-preferably fluorine—and which can be the same or different. The following hydrocarbon residues are cited as example:

methyl, ethyl, propyl, 1-methylethyl (iso-propyl), butyl, 1-methylpropyl, 2-methylpropyl-1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-methylpropyl und 1-ethyl-2-methylpropyl.

Particularly cited as examples are methyl methacrylate, ethyl methacrylate, butyl methacrylate, 2-ethylhexyl methacrylate, methyl acrylate, ethyl acrylate, butyl acrylate and 2-ethylhexyl acrylate or alkyl maleates—such as, for example in particular the methyl maleate.

In addition, it is also possible to use other polymers forming polyanionic structures having, for example, sulphonic or phosphonic acid groups, represented by, for example, polystyrenesulphonic acid or polystyrenephosphonic acid in the form of their homopolymers or as components of copolymers.

With these polymers or copolymers too a part of the sulphonic acid or phosphonic acid groups can optionally be esterified.

In addition the phenyl partial structure of all polymers based on polystyrene optionally can be substituted. Thus, an optionally substituted phenyl group means a phenyl group which optionally independently of one another is substituted with one, two or three substituents selected from alkyl groups (as defined above), haloalkyl residues, halogen atoms (fluorine, chlorine, bromine or iodine), nitro, cyano groups, —OR (whereby R is a hydrogen atom or an alkyl residue), —NRR' (whereby R and R' independently of one another are in each case a hydrogen atom or an alkyl residue), —COOR (whereby R is a hydrogen atom or an alkyl residue) or —CONR'R" (whereby R' and R" independently selected from hydrogen atoms or alkyl residues). Finally, mixtures of all named polymers or copolymers can also be used.

In a preferred embodiment of the present invention, the copolymer able to form a polyanionic structure is typified especially by a carboxylated polymer based on styrene and maleic acid. The copolymer comprises thereby 5 to 95% by weight, preferably 25 to 95% by weight, and particularly preferably 50 to 95% by weight of maleic acid units.

In a further preferred embodiment of the present invention, the copolymer able to form a polyanionic structure is typified by a carboxylated polymer based on methyl vinyl ether and maleic acid.

In the case of all maleic acid/vinyl ether copolymers the vinyl alkyl ether partial structure and also the maleic acid partial structure optionally can be substituted independently of one another with one, two, three or four substituents—relative to the respective monomer—selected from alkyl residues (as defined above), haloalkyl residues, halogen atoms, nitro, cyano groups, —OR (whereby R is a hydrogen atom or alkyl residue), —NRR' (whereby R and R' independently of one another are a hydrogen atom or an alkyl residue), —COOR (whereby R is a hydrogen atom or an alkyl residue or —CONR'R" (whereby R' and R" independently of one another are selected from hydrogen atoms or alkyl residues).

Furthermore, the carboxyl groups in the copolymers—for example in—poly(methyl vinyl ether-alt-maleic acid)

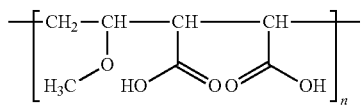

optionally can be totally or partially esterified, preferably by a methyl group.

Also preferably used are
poly(isobutylene-alt-maleic acid) MW: 3.250.000
polystyrene-co-maleic acid, 50% by weight maleic acid
polystyrene-co-maleic acid, 25% by weight maleic acid
polystyrene-co-maleic acid, 14% by weight maleic acid
polyisoprene-graft-maleic acid 7% by weight maleic acid
poly(maleic acid-1-octadec-1-ene) in the molar ratio 1:1
poly(methyl vinyl ether-alt-maleic acid) MW: 1.250.000
polystyrene-alt-maleic acid partially as methyl ester
poly(acryl acid-co-methyl acrylate)
polystyrene sulphonic acid.

According to the invention poly(methyl vinyl ether-alt-maleic acid) copolymers with a molecular weight in a range between $1.0 \times 10^3$ and $2.5 \times 10^6$, preferably $1.0 \times 10^4$ to $2.2 \times 10^6$ and particularly preferably in a range of $1.9 \times 10^6$ to $2.1 \times 10^6$ are used.

Most particularly preferably poly(methyl vinyl ether-alt-maleic acid) [CAS number: 25 15340-6] with a molecular weight of MW=1,980,000 is used.

The preparation of the anionic or carboxylated polymers or copolymers used according to the invention is well known from the state of the art. Since these polymers are already used in a plethora of other technical application, to a large extent they are commercially available.

Further desired polymers or copolymers can be prepared with the methods well-known from the state of the art—e.g. by radical polymerisation with monomers optionally having protected carboxyl groups.

The polyanionic or carboxylated polymers can be applied to the peripheral wall/walls of a suitable reaction vessel in many ways, e.g. in the liquid state, or they can be present in the form of a suspension in the mixture of living or dead cells or in the form of a so-called dipstick.

Thus, coating with a polymer melt can also lead to the desired functionalised layer. There is also the possibility—provided that the reaction vessel is prepared by means of injection moulding—of adding one or more polymer(s) as additive(s) to the mass intended for injection moulding before injection moulding. There is equally the possibility to coat all or certain parts of the injection mould with the polymer(s) prior to injection moulding, whereby the desired coatings are obtained after the formation of the reaction vessel.

Furthermore, there is the possibility to attach a film of the polymers forming the polyanionic structure to the inner wall of the reaction vessel and, for example, to bring into the desired geometric shape by so-called deep draw methods. Preferred in addition is coating with the polyanionic polymer that is dissolved in a suitable solvent.

Furthermore, there is the possibility that at least one polymer is introduced into the solution initially in the form of a so-called precursor, from which the polymer having the desired structure of anionic or carboxyl groups is first formed during the course of the separation procedure.

In addition, there is furthermore the possibility—by selection of suitable polymers known the person of skill in the art—to achieve the desired functionalisation of the surface with known "wet-chemical methods" known from the state of the art (for example sulphuric acid/hydrogen peroxide) or, for example, by atmospheric pressure plasma treatment after preparation of the initially non-functionalised reaction vessel.

In a further embodiment a coating or derivatisation of the vessel surface can be omitted if the polymer able to form polyanionic structures is added to the mixture (see above). The binding of the dead cells does not then take place on a cohesive matrix surface, but directly in the liquid phase. This leads to complexes comprising the dead cells and the carboxylated polymers, which can adhere to the liquid or dispersed matrix. The anionic or carboxylated polymer itself can then, for example, be separated from the liquid phase in a precipitation step after which the living cells located in the liquid phase can be isolated or the polymer with the dead cells is adsorbed, for example, onto the wall of the reaction vessel.

In all embodiments the dead cells remain immobilised on the matrix or on the polymer present in solution, whereas the living cells remain in the liquid phase.

Thus, the method according to the invention for the separation of living cells makes possible not only a significant reduction in the number of working steps, but also ensures a gentle treatment of the of the cells in that it does not rely on the use of toxic substances or the cells are not subjected to high osmotic or ionic loading. Owing to the appreciable reduction in the number of working steps the method according to the invention advantageously can be reduced to a so-called one-step method in which in particular separation steps such as, for example, centrifugation and/or filtration steps can be omitted. In addition also to the time element, cost-intensive consumables such as, for example, centrifugation and/or filtration columns can be saved.

In addition, the method according to the invention has the advantage that owing to its simple operability it is easily automated.

For example, the method according to the invention can be carried out in principle as follows:

A suitable reaction vessel, for example in general a cell culture dish (multi-well plates, blocks or cell culture flasks, for example, can also be used), is incubated with one of the above-described polymer solutions in a suitable solvent, for example an organic solvent or in an aqueous solvent or in an aqueous solvent mixture. The incubation can be carried out thereby at any temperature lying between the solidification temperature of the mixture and its boiling point.

Suitable organic solvents are all common solvents, such as, for example, halogenated hydrocarbons such as, for example, dichloromethane, chloroform or tetrachlorohydrocarbon, alcohols such as, for example, methanol, ethanol, isopropyl alcohol, glycol or glycerol, ethers such as, for example, diethyl ether, glyme or diglyme, anisole, THF or dioxan, ketones such as, for example, acetone, methylethyl ketone or cyclohexanone, esters such as, for example, ethyl acetate, acid amides such as, for example, DMF or HMPT, or sulphoxides, such as, for example DMSO.

In addition aqueous solvents are suitable—preferably solutions of salts such as an aqueous solution of alkali, pseudoalkali or alkaline earth elements, in particular, however, an aqueous ammonium sulphate solution.

A variety of further suitable solvents which can be used depending upon the respective polymer employed and optionally on the material to be coated is known from the state of the art, whereby the polymer or copolymer can be used in the most different concentrations depending on its respective solubility behaviour. Thus, for example, when using poly (methyl vinyl ether-alt-maleic acid) as carboxylated polymer, a solution of, for example, 2 mg/ml of the copolymer in a 1M aqueous ammonium sulphate solution can be used beneficially.

Moreover, mixtures of the aforementioned solvents can be used as a matter of course.

When using the aforementioned poly(methyl vinyl ether-alt-maleic acid) solution, for example, incubation can be carried out at room temperature (ca. 10 to 30° C., preferably at 20° C.) over a period of 5 minutes. Depending on the polymers employed and the material being coated a temperature in any other range over each and every time interval can also be selected.

The solution is then removed and the cell culture dish thus coated is dried optionally at an elevated temperature (30 to 200° C., preferably 40 to 100° C., particularly preferably 40 to 60° C.) or at a correspondingly reduced temperature in vacuum over a sufficiently long period of time—for example at 50° C. over a period of 12 hours. It is understood that the concentration data, temperature and time intervals given here by way of example can be dependent upon each respective polymer used and the solvent and optionally on the nature of the material to be coated, and can be adapted to the respective conditions or varied over wide limits.

In carrying out the cell separation a cell culture—coming, for example, from an electroporation—is mixed with a serum-containing culture medium and transferred to a cell culture dish coated according to the aforementioned method and incubated at a suitable temperature—advantageously at room temperature—for a sufficiently long period of time. Thereafter the cell supernatant is removed.

In respect of this part step it is also understandable that the temperature and time periods reported can be dependent upon the respective coating material used and on the respective conditions prevailing in the culture medium-cell concentration, pH value, etc. used.

The cells isolated can then be passaged further.

The analysis of the cells can be carried out with any suitable determination method, for example by flow cytometry and by microscopy of the retained or non-retained cells.

For example, in flow cytometry the fraction of living cells and also the dead cells can be determined, for example, by staining with propidium iodide.

The figures, which embody an integral part of this patent application show the following:

FIG. 1 represents an uncoated cell culture dish (microscopic image) compared to a plate coated according to the invention FIG. 2 (microscopic image). Both dishes were incubated with a mixture of living and dead cells. Next the supernatant was removed. It is clear from the two microscopic images that the coated cell culture dish—unlike the uncoated dish—has enhancingly adsorbed dead cells together with cell debris.

Figures FIG. 3 to FIG. 5 show three histogrammes of flow cytometry (staining with propidium iodide).

Figure 1:

The subject matter of the present invention is thus a method for the separation of living from dead cells in which the mixture comprising living and dead cells is brought into contact with a coated matrix which can absorb the dead cells and isolates the living cells.

A further aspect of the present invention lies in the fact that the matrix material is present in the solid state on the wall of the reaction vessel or as a dipstick.

A further aspect of the present invention lies in the fact that the matrix material is present in a liquid or dispersed form at the start of the cell separation and after separation is fixed or adsorbed onto the walls of the reaction vessel, or is present in a precipitated or suspended form.

A further aspect of the present invention lies in the fact that the matrix material is a polymer or copolymer or terpolymer able to form a polyanionic structure A further aspect of the present invention lies in the fact that the polymer, copolymer or terpolymer able to form a polyanionic structure is a polycarboxylate or a carboxylated polymer.

A further aspect of the present invention lies in the fact that the polymer, copolymer or terpolymer able to form a polyanionic structure is a carboxylated polymer based on vinyl methyl ether, maleic anhydride, styrene, linear or branched alkenes or acrylic acid and its derivatives.

A further aspect of the present invention lies in the fact that the acrylic acid derivative is embodied by a branched or linear $C_1$-$C_{12}$ alkyl acrylate or methacrylate with one to twelve carbon atoms in the alkanol partial structure.

A further aspect of the present invention lies in the fact that the branched or linear alkyl acrylate or methacrylate is methyl methacrylate, ethyl methacrylate, butyl methacrylate, 2-ethylhexyl methacrylate, methyl acrylate, ethyl acrylate, butyl acrylate and 2-ethylhexyl acrylate.

A further aspect of the present invention lies in the fact that the polymer, copolymer or terpolymer able to form a polyanionic structure has phosphonic acid groups.

A further aspect of the present invention lies in the fact that the polymer, copolymer or terpolymer able to form a polyanionic structure has sulphonic acid groups.

A further aspect of the present invention lies in the fact that the polymer with sulphonic acid groups is polystyrene sulphonic acid or a copolymer/terpolymer with polystyrene sulphonic acid.

A further aspect of the present invention lies in the fact that the copolymer or terpolymer able to form a polyanionic structure is a carboxylated polymer based on polystyrene and maleic anhydride.

A further aspect of the present invention lies in the fact that the copolymer comprises 5 to 95% by weight maleic acid units.

A further aspect of the present invention lies in the fact that the copolymer comprises 25 to 95% by weight maleic acid units.

A further aspect of the present invention lies in the fact that the copolymer comprises 50 to 95% by weight maleic acid units.

A further aspect of the present invention lies in the fact that copolymer or terpolymer able to form a polyanionic structure is a carboxylated polymer based on methyl vinyl ether and maleic acid.

A further aspect of the present invention lies in the fact that the copolymer is poly(methyl vinyl ether-alt-maleic acid).

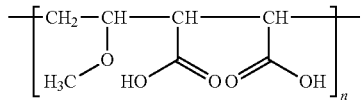

A further aspect of the present invention lies in the fact that the poly(methyl vinyl ether-alt-maleic acid) copolymer has a molecular weight in a range of $1.0 \times 10^3$ to $2.5 \times 10^6$.

A further aspect of the present invention lies in the fact that the poly(methyl vinyl ether-alt-maleic acid) copolymer has a molecular weight in a range of $1.0 \times 10^4$ to $2.2 \times 10^6$.

A further aspect of the present invention lies in the fact that the poly(methyl vinyl ether-alt-maleic acid) copolymer has a molecular weight in a range of $1.9 \times 10^6$ to $2.1 \times 10^6$.

A further aspect of the present invention lies in the fact that within tolerance limits the poly(methyl vinyl ether-alt-maleic acid) copolymer has a molecular weight of $1.980 \times 10^6$.

A further aspect of the present invention lies in the fact that the copolymer poly(methyl vinyl ether-alt-maleic acid) is present as a partial alkyl ester, preferably as $C_1$-$C_6$ alkyl ester and particularly preferably as methyl ester.

A further aspect of the present invention lies in the fact that the reaction vessel is embodied by a Petri dish, a cell culture dish, a multi-well plate, a cell culture flask or blocks.

In addition, the present invention relates to one or more of the aforementioned polymers for cell separation, whereby preferably at least one polymer or copolymer or terpolymer able to form a polyanionic structure is used for the separation of living cell which is particularly preferably a polycarboxylate or a carboxylated polymer based on vinyl methyl ether, maleic anhydride, styrene, linear or branched alkenes or acrylic acid or its derivatives.

If according to a further embodiment of the invention it relates to use of an acrylic acid derivative this embodies advantageously a branched or linear $C_1$ to $C_{12}$ alkyl acrylate or methacrylate with one to twelve, preferably one to six carbon atom(s) in the alkanol partial structure, whereby the branched or linear alkyl acrylate or methacrylate is particularly preferably methyl methacrylate, ethyl methacrylate, butyl methacrylate, 2-ethylhexyl methacrylate, methyl acrylate, ethyl acrylate, butyl acrylate and 2-ethylhexyl acrylate.

According to a further aspect of the invention, the polymer, copolymer or terpolymer able to form a polyanionic structure has phosphonic acid groups or sulphonic acid groups, whereby the polymer having sulphonic acid groups is preferably polystyrene sulphonic acid or a copolymer/terpolymer with polystyrene sulphonic acid.

In a further aspect of the invention, the copolymer or terpolymer able to form a polyanionic structure employed is a carboxylated polymer based on styrene and maleic anhydride, where by the copolymer preferably comprises 5 to 95% by weight, particularly preferably 25 to 95% by weight and most particularly preferably 50 to 95% by weight maleic acid units.

According to a further aspect of the invention, the copolymer or terpolymer able to form a polyanionic structure employed is a carboxylated polymer based on methyl vinyl ether and maleic acid, preferably copolymer poly(methyl vinyl ether-alt-maleic acid),

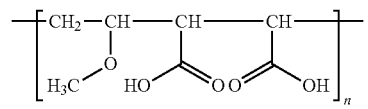

which advantageously has a molecular weight in a range of $1.0 \times 10^3$ to $2.5 \times 10^6$, preferably in a range of $1.0 \times 10^4$ to $2.2 \times 10^6$, particularly preferably in a range of $1.9 \times 10^6$ to $2.1 \times 10^6$, most particularly preferably within tolerance limits a molecular weight of $1.980 \times 10^6$.

According to a further aspect of the present invention the copolymer poly(methyl vinyl ether-alt-maleic acid) employed is present as a partial alkyl ester, preferably as $C_1$-$C_6$ alkyl ester and particularly preferably as methyl ester.

Another subject matter of the present invention relates to a complex comprising dead cells and optionally further cell components and a polymer, copolymer or terpolymer having a polycationic structure.

The invention is further illustrated on the basis of the following examples. These examples embody merely advantageous embodiments of the present invention without restricting it.

EXAMPLES

I Preparation of Different Copolymers

1.) To 50 ml polystyrene-co-maleic acid with a 14% by weight maleic anhydride fraction dissolved in DMSO (20 mg/ml dimethyl sulphoxide) are added 250 mg N-(2-hydroxyethyliminodiacetic acid) and the mixture is heated to 60° C. for a period of 45 min.

After a 10-fold dilution with DMSO a ready-for-use solution for coating reaction vessels for cell separation is obtained.

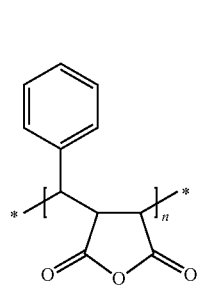 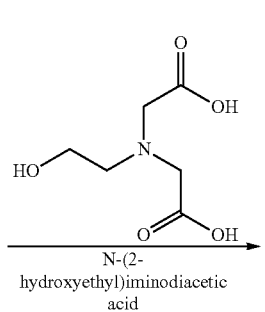 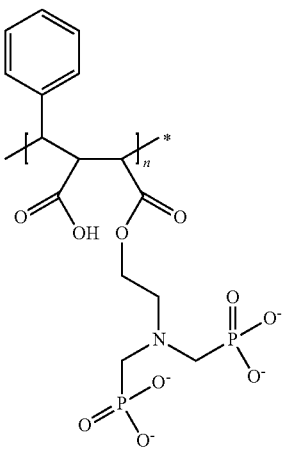

Polystyrene-co-maleic anhydride    N-(2-hydroxyethyl)iminodiacetic acid

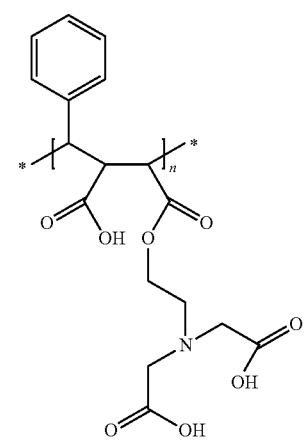

2.) To 50 ml polystyrene-co-maleic acid with a 50% by weight maleic anhydride fraction dissolved in DMSO (20 mg/ml dimethyl sulphoxide) are added 1.3 g N-(2-hydroxyethyl)iminobis(methylphosphonic acid) and the mixture is heated to a temperature of 60° C. for a period of 1 h. After a 10-fold dilution with DMSO a ready-for-use solution for coating reaction vessels for cell separation is obtained.

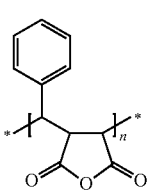 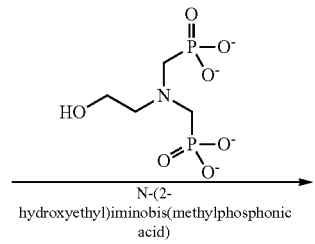

Polystyrene-co-maleic anhydride    N-(2-hydroxyethyl)iminobis(methylphosphonic acid)

3.) 50 mg (0.877 mmol) N-Me-PVA (N-methyl-polyvinylamine) were dissolved in 2 ml water and after the addition of 1.31 mmol bromoacetic acid (180 mg, 1.5 eq) and 50 µl TEA (triethylamine) were shaken for a period of 12 h. In this way a ready-for-use solution for coating reaction vessels for cell separation is obtained.

4.) 0.2 g Polyvinyl alcohol (MW 9000-10000) were treated with 630 mg (0.454 mmol, 0.8 eq.) bromoacetic acid and after the addition of 1.2 g $K_2CO_3$ (9.08 mmol, 1.5 eq.) were shaken for 12 h. A ready-for-use solution for coating reaction vessels for cell separation is obtained.

II Carrying Out the Coating

1.) 20 mg Poly(methyl vinyl ether-alt-maleic acid) were dissolved in 10 ml deionised water. After the polymer had dissolved completely 50 µl each time of the aqueous polymer solution were pipetted into commercial polypropylene 6-well plates. After 20 min incubation time at room temperature the aqueous polymer solution was pipetted from the vessels. The vessels were then washed once with 120 µl water and dried at 40° C.

2.) A cell culture dish (well) was incubated with 400 µl of a solution of poly(methyl vinyl ether-alt-maleic acid) (2 mg/ml) in a 1 M aqueous ammonium sulphate solution at room temperature (20° C.) for a period of 5 min. The solution was then removed and the coated cell culture dish was dried at a temperature of 50° C. for a period of 12 h.

III Cell Separation after Electroporation

1.) Suspension cells were used as cell material. 200,000 K562 cells (human myeloid leukaemia cell line) were washed with 200 µl of a serum-free culture medium and electroporated in 200 µl of a serum-free culture medium in an electroporator from the company BioRad® according to the company's directions for the transfection of K562 cells. After the addition of 400 µl of a medium containing 13.3% FCS the mixture thus obtained was transferred to the wells of a 6-well plate coated as described in Example II 2, following which addition of 1 ml of serum-containing medium was carried out. After incubation over a period of 5 min at room temperature the supernatant was removed and its analysis carried out.

Figure 2:
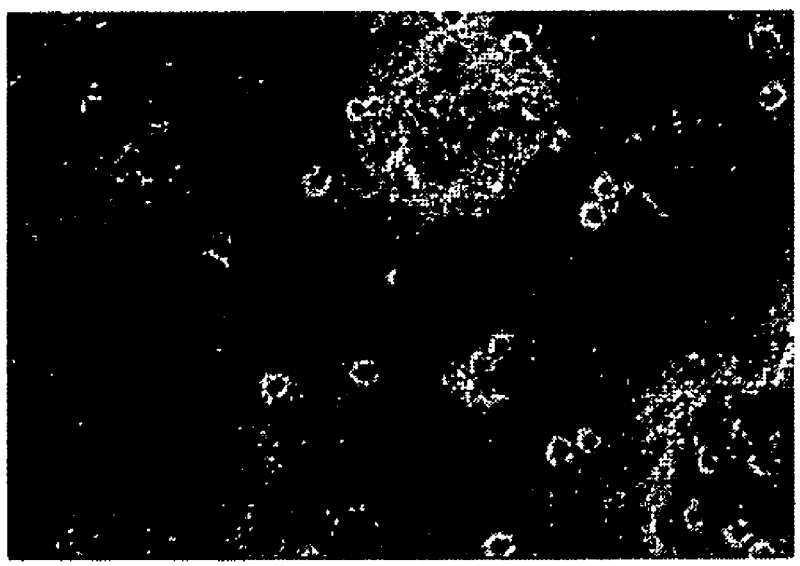

Microscopic analysis showed that a cell culture dish coated as described in Example II 2 (FIG. 1, first microscopic image) had immobilised significantly more dead cells and cell debris in comparison to the uncoated plate (FIG. 2, second microscopic image).

Figure 3:
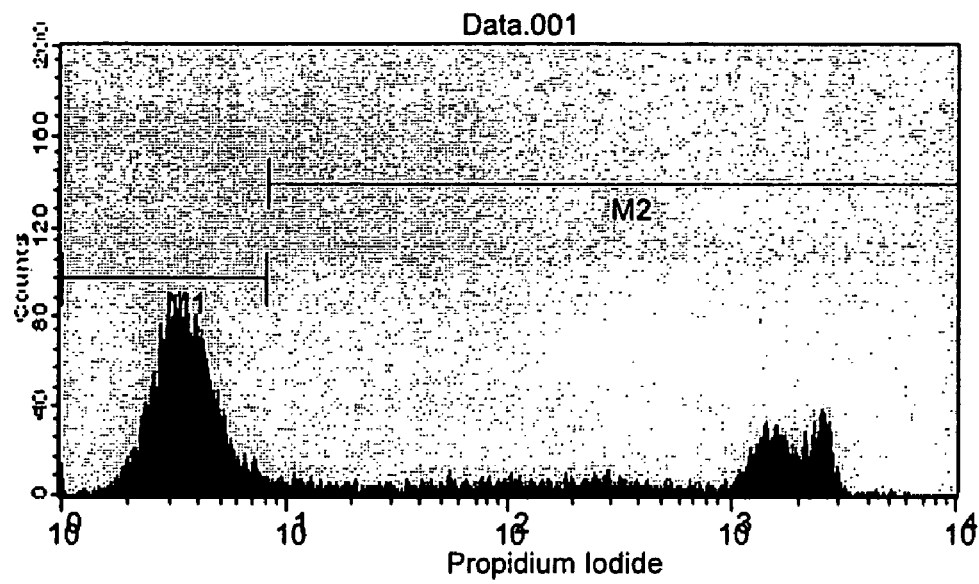
FIG. 3 shows a histogramme of untreated cells.
Figure 4:
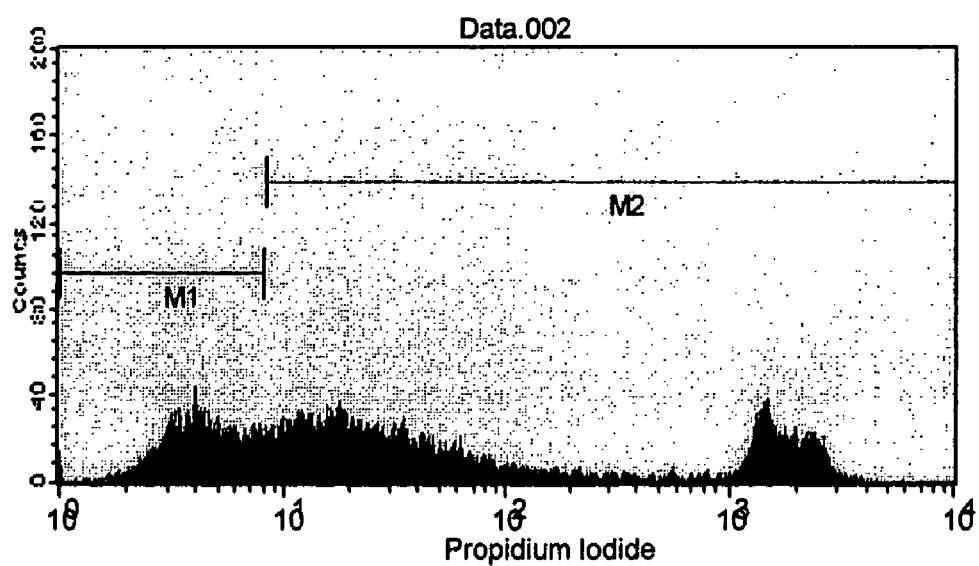
FIG. 4 illustrates the histogramme of the cells after electroporation.
Figure 5:
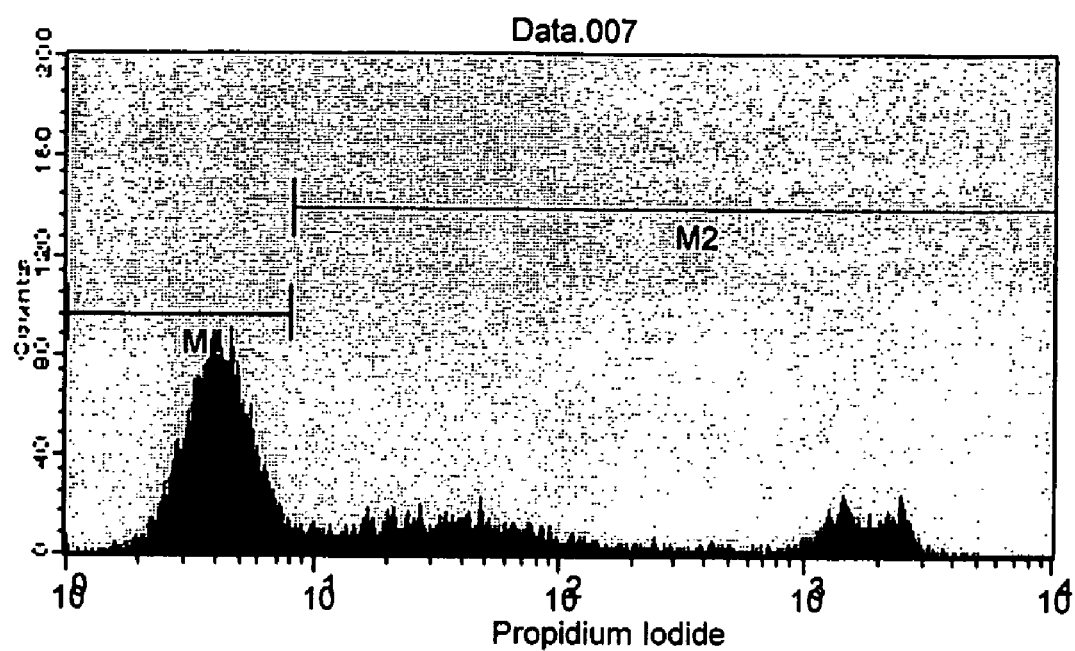
FIG. 5 shows in conclusion the corresponding histogramme of the cells-purified according to the invention.

The results of the flow cytrometry are shown as follows:

The percentage of living cells was calculated on the basis of the "Gate M1" in the histogrammes shown in FIGS. 3, 4 and 5.

The result is shown in the following Table 1:

TABLE 1

| Type of cells | % living cells |
| --- | --- |
| Untreated cells | 64 |
| Cells after electroporation | 36 |
| Purified cells | 63 |

It can be seen from the experimental results that the fraction of living cells falls after electroporation from 64% to 36%, whereas the percentage of living cells after purification has at 63% once more achieved approximately the original value.

The purified cell population is thus qualitatively once more comparable to the original cells before electroporation.

2.) Here too suspension cells were used as cell material. 200 000 K562 cells (human myeloid Leukaemia cell line) were washed with 200 µl of a serum-free culture medium and electroporated in 200 µl of a serum-free culture medium in an electroporator from the company BioRad® according to the company's directions for transfection of K562 cells. After the addition of 400 µl a medium containing 13.3% FCS the mixture thus obtained was transferred to the wells of a 6-well plate coated as described in Example II 2, after which the addition of 1 ml of serum-containing medium was carried out. After incubation over a period to 5 min at room temperature the supernatant was removed and its analysis carried out.

Figure 6:
FIG. 6 represents a microscopic image of a cell culture dish after removal of the supernatant that was treated with the aforementioned method and is coated with dead cells and cell debris.

The microscopic (third) images reproduced in FIG. 6 shows that in this experiment too the coated cell culture dish adsorbed and retained the dead cells in addition to the cell debris.

The percentage of living cells was carried out by flow cytometry in a manner analogous to the previously described first experiment and showed the results given in Table 2:

TABLE 2

| Type of cells | % living cells |
| --- | --- |
| Untreated cells | 77 |
| Cells after electroporation | 31 |
| Purified cells | 56 |

It can be seen from the experimental results that the fraction of living cells falls after electroporation from 77% to 31%. After purification the percentage of living cells again rose significantly to 56%. In this experiment too the quality of the cell population is significantly improved after purification.

The invention claimed is:

1. A method for the separation of living eukaryotic cells from dead eukaryotic cells, comprising contacting a mixture comprising the living eukaryotic cells and the dead eukaryotic cells with a matrix material comprising a poly(methyl vinyl ether-alt-maleic acid):

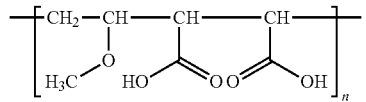

that is able to form a polyanionic structure, wherein the dead eukaryotic cells adsorb onto the matrix material and the living eukaryotic cells do not adsorb onto the matrix material.

2. The method according to claim 1, wherein the matrix material is present in a solid state on a wall of a reaction vessel or a dipstick.

3. The method according to claim 2, wherein the matrix material is present in a liquid or disperse state prior to separation and after separation is fixed or adsorbed to the reaction vessel or dipstick, or is present in precipitated or suspended form.

4. The method according to claim 1, wherein the poly (methyl vinyl ether-alt-maleic acid) has been esterified to a partial alkyl ester.

5. The method according to claim 1, wherein the reaction vessel is a Petri dish, a cell culture dish, a multi-well plate, a cell culture bottle or blocks.

6. The method of claim 4, wherein the poly(methyl vinyl ether-alt-maleic acid) has been esterified to a $C_1$-$C_6$ alkyl ester.

7. The method of claim 6, wherein the poly(methyl vinyl ether-alt-maleic acid) has been esterified to a methyl ester.

* * * * *